(12) United States Patent
Friedman et al.

(10) Patent No.: US 6,303,750 B1
(45) Date of Patent: Oct. 16, 2001

(54) CONSERVED T-CELL RECEPTOR SEQUENCES

(75) Inventors: Steven M. Friedman, Tenafly, NJ (US); Mary K. Crow; Yixin Li, both of New York, NY (US); Joseph R. Tumang, Woodhaven; Guang-Rong Sun, New York, both of NY (US)

(73) Assignee: New York Society for the Ruptured and Crippled Maintaining the Hopital for Special Surgery, New York, NY (US)

( * ) Notice: Subject to any disclaimer, the term of this patent is extended or adjusted under 35 U.S.C. 154(b) by 0 days.

(21) Appl. No.: 09/543,513

(22) Filed: Apr. 6, 2000

Related U.S. Application Data

(62) Division of application No. 08/963,121, filed on Oct. 28, 1997, now Pat. No. 6,084,087, which is a continuation of application No. 08/427,009, filed on Apr. 24, 1995, now abandoned, which is a division of application No. 08/229,285, filed on Apr. 18, 1994, now abandoned, which is a continuation-in-part of application No. 07/766,751, filed on Sep. 27, 1991, now Pat. No. 5,480,895.

(51) Int. Cl.[7] .......................... C07K 14/725; C12N 15/12
(52) U.S. Cl. .......................... 530/324; 530/326; 530/330; 536/23.1; 536/23.5
(58) Field of Search .................................. 530/324, 326, 530/330; 536/23.1, 23.5

(56) References Cited

PUBLICATIONS

Grom et al. Proc. Natl. Acad. Sci. USA 90, 11104–11108, Dec. 1993.
Howell et al. (1991) Proc. Natl. Acad Sci. USA 88, 10921–10925.
Lunardi et al. (1992) Clin. Exp. Immunol. 90, 440–446.
Zwillich et al. (1994) DNA and Cell Biol. 13, 923–931.
Jenkins et al. (1993) J. Clin Invest. 92, 2688–2701.
Struyk et al. (1994) Intl. Immunol. 6, 897–907.
Pinschke et al. (1991) Eur. J. Immunol. 21, 2749–2751.
Paliard et al. (1991) Science 253, 325–329.
Friedberg et al. J. Bacteriology, vol. 171, No. 11, pp. 6069–6076, 1989.
Kuhnel et al. Proc. Natl. Acad. Sci. USA vol. 86, pp. 2383–2387, 1989.
Yayon et al. The EMBO Journal vol. 11, No. 5, pp. 1885–1890, 1992.

*Primary Examiner*—Prema Mertz
(74) *Attorney, Agent, or Firm*—Darby & Darby

(57) ABSTRACT

Four unique transcripts have been isolated from the β chain of the T cell receptor in T cells in the synovial tissue of a patient with rheumatoid arthritis. Two of these transcripts were isolated from fresh synovial tissue and two were isolated from a T cell line derived from the synovial tissue. The sequences of the four transcripts are highly homologous, with a conserved amino acid sequence of IGQ_N in the highly diverse V-D junction. The α chain and the antigenic specificity of the T cell line derived transcripts has also been characterized.

7 Claims, 9 Drawing Sheets

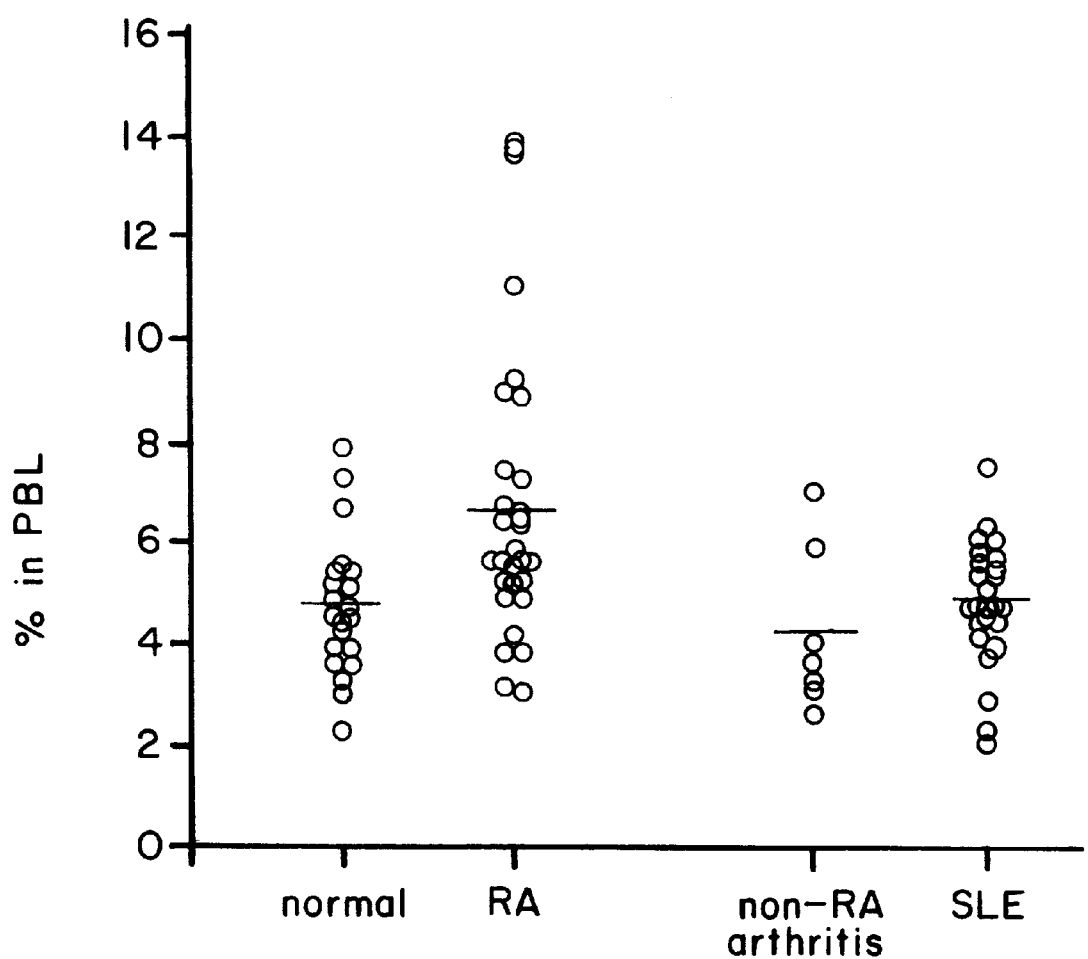

FIG. 4

|  | ---- Vβ ---- | ---- N-D-N ---- | ---------- Jβ ---------- |
|---|---|---|---|
| Vβ17seq1 (STTC, Jβ2.7) | C A S S<br>TGTGCCAGTAGT | I G Q E N<br>ATTGGTCAGGAGAAC | Y E Q Y F G P G T R L T V T<br>TACGAGCAGTACTTCGGGCCGGGCACCAGGCTCACGGTCACA |
| Vβ17seq2 (STTC, Jβ2.1) | C A S S<br>TGTGCCAGTAGT | I Q G<br>ATACAGGGG | Y N E Q F F G P G T R L T V L<br>TACAATGAGCAGTTCTTCGGGCCAGGGACACGGCTCACCGTGCTA |
| Vβ17seq3 (Cult 5, Jβ2.1) | C A S S<br>TGTGCCAGTAGT | I G Q T<br>ATCGGGCAGACG | N E Q F F G P G T R L T V L<br>AATGAGCAGTTCTTCGGGCCAGGGACACGGCTCACCGTGCTA |
| Vβ17seq4 (Cult 5, Jβ2.1) | C A S S<br>TGTGCCAGTAGT | I P R A<br>ATACCCCGGGCC | N E Q F F G P G T R L T V L<br>AATGAGCAGTTCTTCGGGCCAGGGACACGGCTCACCGTGCTA |

FIG. 5

(A) Vα2.3-Jα (IGRJα09)-Cα

```
--- Vα --    -- V-J --                      ---------- Jα ----------
  C   V   V    K   G   G                G   N   K   L   V   F   G   A   G   T   I   L   R   V   K   S   Y    ---- Cα ----    I   Q   N   P
TGTGTGGTG   AAGGGAGGG              GGAAACAAGCTGGTCTTTGGCGCAGGAACCATTCTGAGAGTCAAGTCCTAT                   ATCCAGAACCCT
```

(B) Vα3.1-Jαk-Cα

```
-- Vα ---     -V-J-                         ---------- Jα ----------
  C   A   T     L                 G   G   S   N   Y   K   L   T   F   G   K   G   T   L   L   L   T   V   N   P   N    ---- Cα ----    I   Q   N   P
TGTGCTACA   CTG               GGAGGTAGCAACTATAAACTGACATTGGAAAAGGAACTCTTACCGTGAATCCAAAT                   ATCCAGAACCCT
```

CONSERVED T-CELL RECEPTOR SEQUENCES

This is a division of application Ser. No. 08/963,121, filed Oct. 28, 1997 now U.S. Pat. No. 6,084,087, which is a continuation of application Ser. No. 08/427,009, filed Apr. 24, 1995 now abandoned, which is a division of Ser. No. 08/229,285, filed Apr. 18, 1994, now abandoned which is a CIP of Ser. No. 07/766,751, filed Sep. 27, 1991 now U.S. Pat. No. 5,480,895.

BACKGROUND OF THE INVENTION

T lymphocytes recognizes antigens through the T cell antigen receptor (TCR) complex. The TCR is a clone-specific heterodimer on T cells, which recognizes its target antigen in association with a major histocompatibility antigen. Moreover, the TCR is highly polymorphic in different T cells. Approximately 90 percent of peripheral blood T cells express a TCR consisting of an α polypeptide and a β polypeptide and a small percentage of T cells express a TCR consisting of a γ polypeptide and a δ polypeptide. See Davis and Bjorkman, 1988, *Nature* 334:395–402; Marrack and Kappler, 1986, *Sci. Amer.* 254:36; Meuer et al., 1984, *Ann. Rev. Immunol.* 2:23–50; Brenner et al., 1986, *Nature* 322:145–159; Krangel et al., 1987, *Science* 237:1051–1055; Hata et al., 1987, *Science* 238:678–682; Hochstenbach et al., 1988, *J. Exp. Med.* 168:761–776).

The chains of the T cell antigen receptor of a T cell clone are each composed of a unique combination of domains designated variable (V), diversity (D), joining (J), and constant (C) (Siu et al., 1984, Cell 37:393; Yanagi et al., 1985 *Proc. Natl. Acad. Sci. USA* 82:3430). Hypervariable regions also have been identified (Patten et al., 1984, *Nature* 312:40; Becker et al., 1985, *Nature* 317:430). In each T cell clone, the combination of V, D and J domains of both the alpha and the beta chains or both the delta and gamma chains and defines a unique antigen binding site in each T-cell clone. In contrast, the C domain does not participate in antigen binding.

TCR genes, like immunoglobulin genes, consist of regions which arrange during T cell ontogeny (Chien et al., 1984, *Nature* 312:31–35; Hedrick et al., 1984, *Nature* 308:149–153; Yanagi et al., 1984, *Nature* 308:145–149). In genomic DNA, each TCR gene has V, J, and C regions; TCR β and δ polypeptides also have D regions. The V, D, J and C regions are separated from one another by spacer regions in the DNA. There are usually many variable region segments and somewhat fewer diversity, junctional, and constant regions segments. As a lymphocyte matures, these various segments are spliced together to create a continuous gene sequence consisting of one V, (D), J, and C regions. TCR diversity, and thus T cell specificity, derives from several sources, (Barth et al, 1985, *Nature* 316:517–523; Fink et al., 1986, *Nature* 321:219–225) including: a multiplicity of germline gene segments (Chien et al., 1984, *Nature* 309:322–326; Malissen et al., 1984, *Cell* 37:1101–1110; Gascoigne et al., 1984, *Nature* 310:387–391; Kavaler et al., 1984, *Nature* 310:421–423; Siu et al., 1984, *Nature* 311:344–349; Patten et al., 1984, *Nature* 312:40–46), combinatorial diversity through the assembly of different V, D, J, and C segments (Siu et al., 1984, *Cell* 37:393–401; Goverman et al., 1985, *Cell* 40:859–867), and junctional flexibility, N-region diversity and the use of either multiple D regions or any of the three translational reading frames for Dβ segments. As a result of these mechanisms, TCRs are generated which differ at their N-terminal (called variable, or V regions, constructed from combinations of V, D, and J gene segments) but are the same elsewhere, including their C-terminal (called constant regions). Therefore, an infinite number of TCRs can be established.

The Vβ gene of the TCR appears to resemble most closely the immunoglobulin V gene in that it has three gene segments, Vβ, Dβ, and Jβ, which rearrange to form a contiguous Vβ gene (Siu et al., 1984, *Cell* 37:393–401). The β locus has been well characterized in mice, where it spans 700–800 kilobases of DNA and is comprised of two nearly identical C regions tandemly arranged with one D element and a cluster of 5–6 J elements 5' to each (Kronenberg et al., 1986, *Ann Rev. Immunol.* 3:537–560). Approximately twenty to thirty Vβ regions are located upstream (5') to the D, J, and C elements (Behlke et al., 1985, *Science*, 229:566–570) although Vβ genes may also be located 3' to the murine Cβ genes (Malissen et al., 1986, *Nature* 319:28). Study of the structure and diversity of the human TCR β-chain variable region genes has led to the grouping of genes into district Vβ subfamilies (Tillinghast et al., 1986, *Science* 233:879–883; Concannon et al., 1986, *Proc. Natl., Acad. Sci. USA* 83:6598–6602; Borst et al., 1987, *J. Immunol.* 139:1952–1959).

The γTCR gene was identified, first in mice (Saito et al., 1984, *Nature* 309:757–762; Kranz et al., 1985, *Nature* 313:762–755; Hayday et al., 1985, *Cell* 40:259–269) and then in humans (Lefranc et al., 1985, *Nature* 316:464–466; Murre et al., 1985, *Nature* 316:549–552). The human γTCR locus appears to consist of between five and ten variable, five joining, and two constant region genes (Dialynas et al., 1986, *Proc. Natl. Acad. Sci. USA* 83:2619).

The TCR α and δ locus are adjacent to one another on human chromosome 14. Many TCR δ coding segments are located entirely within the α gene locus (Satyanarayana et al., 1988, *Proc. Natl. Acad. Sci. USA* 85:8166–8170 Chien et al., 1987, *Nature* 330:722–727; Elliot et al., 1988, *Nature* 331:627–631). It is estimated that there are a minimum of 45–50 Vα regions (Becker et al., *Nature* 317:430–434) whereas there are only approximately 10 Vδ regions (Chien et al., 1987, supra). Nucleic acid sequences of TCR α genes have been reported (Sim et al., 1984, *Nature* 312:771–775; Yanagi et al., 1985, *Proc. Natl. Acad. Sci. USA* 82:3430–3434; Berkout et al., 1988, *Nucl. Acids Res.* 16:5208).

Rheumatoid arthritis (RA) is a chronic, recurrent, inflammatory disease primarily involving joints, affecting 1–3% of North Americans. Three times the number of women are afflicted with RA than men. Severe RA patients tend to exhibit extra-articular manifestations including vasculitis, muscle atrophy, subcutaneous nodules, lymphadenopathy, splenomegaly and leukopenia. Spontaneous remission may occur; other patients have brief episodes of acute arthritis with longer periods of low-grade activity; still others progress to severe deformity of joints. It is estimated that about 15% of RA patients become completely incapacitated ("Primer on the Rheumatic Diseases," 8th edition, 1983, Rodman, G. P. & Schumacher, H. R. Eds., Zvaifler, N. J., Assoc. Ed., Arthritis Foundations, Atlanta, Ga.).

The antigenic stimulus initiating the immune response and consequent inflammation is unknown. Certain HLA types (DR4, Dw4, Dw14 and DR1) have an increased prevalence of RA, perhaps leading to a genetic susceptibility to an unidentified factor which initiates the disease process. Relationships between Epstein Barr virus and RA have been suggested.

Many cell types, notably macrophages, synoviocytes and polymorphonuclear leukocytes, participate in the complex inflammatory response which effects joint destruction in R.A. However, a central role for T lymphocytes is suggested by: 1) the rich infiltration of activated T cells at the primary site of RA disease, the synovial tissue van Boxel, J. A., et al., 1975; *N. Engl. J. Med.*, 293:517; Panayi, J. S. et al., 1992, *Arthritis Rheum.* 35:729; 2) genetic studies linking RA disease susceptibility to a defined amino acid sequence in the third hypervariable region of the DRβ chain of the major histocompatibilty complex (MHC) class II molecule P. Gregersen, J. Silver, R. J. Winchester, 1987, *Arthritis Rheum.* 30:1205); 3) animal models of chronic arthritis in which antigen-specific T cells are capable of transferring disease to naive recipients R. Holmdahl, L. Klareskog, K. Rubin, E. Larsson, H. Wigzell, *Scand. J. Immunol.* 22:295 (1985); W. van Eden et al., *Proc. Natl. Acad. Sci. USA*, 1985, 82:5117 (1985)); and 4) amelioration of arthritis, both in murine models of autoimmune disease and in patients with RA, by administration of monoclonal antibody (mAb) reactive with the CD4+T cell subset G. E. Rangers, S. Sriram, S. M. Cooper, *J. Exp. Med.*, 1985, 162:11104; G. Horneff, G. R. Burmester, F. Emmrich, J. R. Kalden, *Arthritis Rheum.*, 1991, 34:129).

Previous studies designed to correlate TCR structure with antigen-MHC molecular complex recognition have emphasized the importance of critical amino acid residues in each of the three polymorphic CDR regions of both α and β chains, with CDR3 playing a dominant role. In both the murine and human systems, T cells specific for a particular peptide—MHC complex often utilize a characteristic amino acid or sequence cluster in the CDR3 region (S. M. Hedrick et al., *Science*, 1988, 239:1541). Recent studies demonstrate that the introduction of charge altering amino acids in a well defined antigenic peptide results in a T cell response characterized by antigen-specific TCRs which have incorporated reciprocal charge changes in the CDR3 amino acid residues of both α and β chains (J. L. Jorgensen et al., *Nature*, 1992, 355:224). This result suggests that these TCR residues bind directly to the antigenic peptide. In a related study, it was found that the murine TCR repertoire recognizing foreign peptides which are highly homologous to self is markedly constrained with respect to TCR Vα and Vβ gene usage, CDR3 length, and the presence of canonical amino acid residues in the CDR3 domain (J. -L. Casanova et al., *J. Exp. Med.*, 1991, 174:1371). These data suggest that pathogenic T cells mediating autoimmune disease will express TCR which share crucial structural characteristics.

Further support for this hypothesis is found in studies of other autoimmune diseases. Myelin basic protein (MBP) specific $T_h$ cells induce experimental allergic encephalomyelitis (EAE) S. S. Zamvil et al., *J. Exp. Med.*, 1988, 167:1586; J. L. Urban at al., *Cell*, 1988, 54:577; F. R. Burns et al., *J. Exp. Med.*, 1989, 169:27). Encephalitogenic T cell clones are strongly biased with respect to Vβ and Vα gene usage as well as CDR3 region structure (D. P Gold et al., *J. Immunol.*, 1992, 148:1712). Recently, it has been shown that TCR Vβ transcripts isolated from central nervous system lesions of patients with multiple sclerosis (MS) exhibit sequence motifs in the CDR3 region homologous with those expressed by encephalitogenic MBP reactive murine T cell clones (R. Martin et al., *J. Exp. Med.*, 1991, 173:19; J. R. Oksenberg et al., *Nature* 362, 1993, 68).

While the importance of T cells in RA appears clear, neither the antigen specificity nor the structure of the TCR expressed by disease-inducing T cells has been determined. In an attempt to identify pathogenic T cells among the vast number present in the inflamed joint, investigators have applied molecular techniques to detect T cells which: 1) share TCR structural features, i.e. restricted usage of particular TCR variable gene elements, or 2) are "oligoclonall" with respect to the highly polymorphic antigen binding CDR3 region of the TCR, suggesting antigen-driven expansion at the site of pathology. To date, this approach has yielded conflicting results. Several laboratories have reported evidence of oligoclonality and over-usage of particular TCR V gene products among RA joint-derived T cells (M. D. Howell et al., *Proc. Natl. Acad. Sci. USA*, 1991, 88:10921; X. Paliard et al., *Science*, 1991, 253:325; W. V. Williams et al., *J. Clin. Invest.*, 1992, 90:326). However, the TCR V gene families implicated vary from study to study and still other investigations find no evidence for TCR skewing in RA Y. Uematsu et al., *Proc. Natl. Acad. Sci. USA*, 1991, 88:8534; J. M. van Laar et al., *Clin. Exp. Immunol.*, 1991. 83:353).

SUMMARY OF INVENTION

Pour unique Vβ 17 transcripts encoding conserved CDR3 regions of the T cell receptor of RA patients has now been discovered. These unique transcripts while not identical, are highly homologous in an otherwise variable region of the TCR. Also, within these transcripts is a highly conserved sequence IGQ_N (sequence I.D. No.13). These transcripts were isolated from the synovial tissue of a RA patient and a cell line expanded from synovial tissue T-cells.

It has also been discovered that two unique α chains with conserved CDR3 sequences are utilized by the unique T cell clones.

Methods for diagnosing and treating RA with the peptides encoded by the transcripts and/or monoclonal antibodies specific for the peptides is also part of this invention.

DESCRIPTION OF THE FIGURES

FIGS. 1A and 1B depicts mononuclear cells (MNC) from healthy subjects, patients with seropositive RA, patients with non-RA inflammatory arthritis, and patients with systemic lupus erythematosus (SLE) that were analyzed by indirect immunofluorescence for expression of Vβ 17 TCR gene products. Results for peripheal blood (PB) are shown in FIG. 1B panel and for synovial fluid (SF) in FIG. 1B and are expressed as % of cells reactive with the anti-TCR Vβ mAb/% of cells reactive with anti-CD3 mAb.

FIG. 4 depicts the CDR3 sequences of dominant Vβ7 transcripts identified among freshly isolated synovial tissue T cells (Vβ17seq1 and seq2) and culture 5 derived T cell clones expanded in vitro (Vβ17seq3 and seq4). The conserved amino acid residues at the N-D-N area are presented in boldface.

FIG. 5 depicts the nucleotide and deduced amino acid sequences in the CDR3 regions for Vα2.3 (A) and Vα3.1 (B). The Vα2.3, containing a Jα(IGRJaO9) segment, accompanys Vα17seq3 and the Vα3.1, using a Jαk segment, is linked to Vβ17seq4 expressing in culture 5-derived T cell clones.

DETAILED DESCRIPTION OF THE INVENTION

Figure 1B:
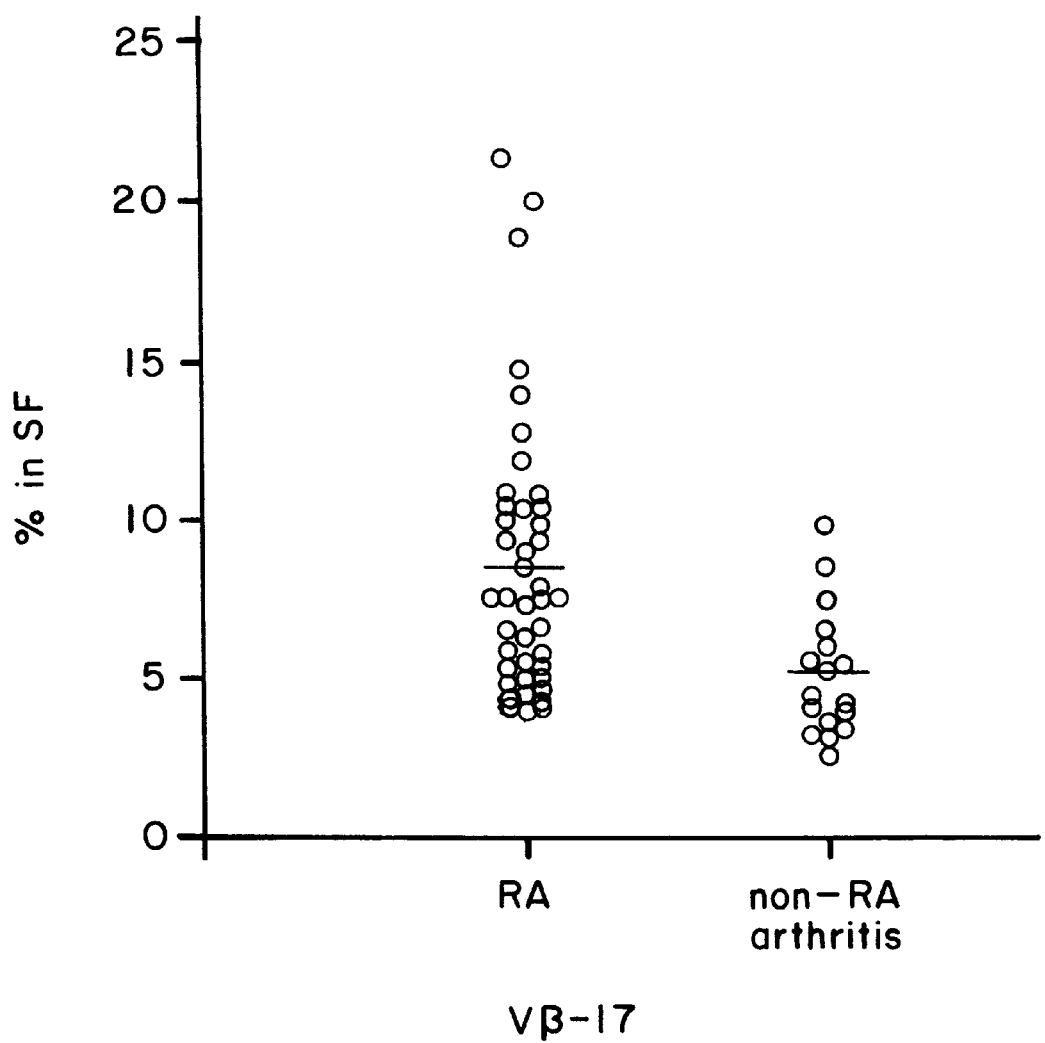

The invention is directed to unique α/β T cell receptor (TCR) sequences which are conserved in the synovial tissue of persons afflicted with RA. These four sequences show sequence homology in the complementarity-determining-region (CDR3), which is normally a highly variable region of the TCR. Both the α and β chains of these transcripts have been characterized, as well as their antigenic specificity.

The first step in isolating these transcripts was to identify the type of T cell which is pathogenic in RA and characterize the relevant antigens that maintain their chronic activation. This was done by utilizing a panel of murine mAb reactive with the products of particular TCR Vβ gene families. The results demonstrated the selective increase in the percentage of T cells bearing the Vβ17 TCR sequence in the peripheral blood (PB) and synovial fluid (SF) from patients with RA.

In order to evaluate the pathogenic potential of the oligoclonal Vβ17 synovial T cells, isolation of these cells in vitro and characterization of the TCR α/β chain structure and antigenicity had to be done. To accomplish this, one patient with "classic" RA was followed for eighteen months and then T cells were explanted from his synovium. The unique transcripts were isolated from both the fresh synovium T cells and a cell line generated from the synovial tissue T cells.

Two of these transcripts, designated Vβ17seq1 (seq. I.D. No. 1 and seq. I.D. No.2) and Vβ17seq2 (seq. I.D. No. 3 and seq. I.D. No. 4), were isolated from Vβ17 cDNA clones derived from fresh synovial tissue. The other two of these sequences, designated Vβ17seq3 (seq. I.D. No. 5 and seq. I.D. No. 6) and Vβ17seq4 (seq. I.D. No. 7 and seq. I.D. No. 8) were isolated from a cell line generated in vitro from synovial tissue T cells.

These four transcripts, while not identical, contain highly homologous sequences. The nucleotide and deduced amino acid sequences in the CDR3 region are shown in FIG. 4.

Comparison of the sequences show that amino acid residue "I" at position 95 and "N" at position 99 is found in all four transcripts. It should be noted that residue N at position #99 is encoded by the germline Jβ2.1 segment in Vβ17seq2, 3 and 4 but the same residue in Vβ17seq1 is not germline encoded but results from the process of N region nucleotide addition which generates diversity in the antigen binding VDT region. See Lieber, M. R. et. al., *Proc. Nat'l. Acad. Sci. USA*, 1988, 85:8588.

Furthermore, homology of the sequences of transcripts Vβ17seq1 and Vβ17seq3, in the CDR3, region is 78.5% at the nucleotide level and 86.4% at the amino acid level. Also, 4 out of 5 amino acids, IGQ_N, at residues #95–99, in the highly diverse V-D junction, are conserved in both transcripts.

Without being bound by any theory, it is believed that the four dominant transcripts recognize the same joint-localized antigen and that the conserved amino acids, "I" at position #95 and "N" at position #99 in the CDR3 region of the TCRβ chain may prove crucial for antigen recognition.

Because antigen recognition is a function of both TCR α and β, the α chain usage of the cell line derived T-cell clones characterized also (FIG. 5). Vβ17seq3 expresses the Vα2.3, and had an α rearrangement of Vα2.3-Jγ (IGRJa09)-Cα (seq. I.D. No. 9 and seq. I.D. No. 10). The expression of Vα2.3 is of interest because recent reports have shown a selective increase in Vα2.3 T cells in the synovial fluid of RA patients. See Pluschke, G. et al., *Eur. J. Immunol.*, 1991, 21:749; Bröker, B. M. et al., *Arthritis Rheum.*, 1993, 9:1234. Vβ17seq4 expressed Vα3.1-JαK-Cα (seq. I.D. No. 11 and seq. I.D. No. 12) (FIG. 5).

Lastly, the antigen specificity of the culture derived T cell clones was determined. The synovial T cells expressing the conserved CDR3 sequences respond to the alleles of the PA associated DR4 molecule.

These T cell clones which utilize the same Vβ gene, are highly homologous in the antigen binding CDR3 region, and are reactive with or restricted by the HLA DR4 antigen probably have pathogenic potential in the rheumatoid process. This is supported by: 1) mAb staining results in which only RA, but not other arthropathies, is characterized by an expansion of Vβ17+ T cells; 2) data from other laboratories demonstrating the selective representation of Vβ17, 14 and 3 among RA synovial T cells (Howell, M. D. et al., *Proc. Nat'l. Acad. Sci. USA*, 1991, 88:10921; Paliard et al., *Science*, 1991, 253:325; Williams, W. V., et al., *J. Clin. Invest.*, 1992, 90:326); and most compelling, 3) a CDR3 sequence highly homologous to that in our Vβ17seq2 ("IQG_N") has been identified among the expanded, oligoclonal Vβ14 TCR transcripts isolated from synovial fluid and tissue T cells of a DR4+, RF+ patient suffering from juvenile rheumatoid arthritis. See Grom et al., *Proc. Nat'l. Acad. Sci. USA*, 1993, 90:11104.

The isolation and in vitro growth of clones expressing TCR sequences homologous to the dominant Vβ17 sequences identified in fresh synovium have allowed elucidation of the complete structure of the α β TCR expressed by potentially pathogenic RA T cells. These clones can also be used to assess reactivity against a panel of potentially important self antigens, including joint-restricted antigens postulated to be targets of autoimmune attack, e.g. type II collagen, proteoglycans, heat shock proteins, as well as an array of synthetic peptides containing the sequence shared by RA-associated DR molecules, QKRAA (seq. I.D No. 14).

These sequences could also be used as a confirmatory diagnostic tool for RA. A diagnosis of RA may be made based upon clinical features and a in vitro assay using probes homologous to the conserved TCR sequences could confirm that the patient is indeed suffering from RA, as opposed to other diseases affecting the joints. Such a method would entail contacting the bodily fluid of a person suspected of suffering from RA with a probe homologous to the conserved TCR sequences. Bodily fluid would include, but not be limited to, synovial fluid. The presence or absence of the conserved TCR sequence determined by any method known to those skilled in the art. Specific embodiments would include probes homologous to any one of the CDR3 sequences of Vβseq1, Vβ17seq2, Vβ17seq3 and Vβ17seq4 or other portions thereof. Another preferred embodiment would include probes homologous to the conserved CDR3 α-chain sequences. Yet another preferred embodiment would be a probe homologous to the nucleotide sequence encoding the amino acid sequence IGQ_N.

The unique TCR sequences could also be used for immunotherapy for RA, for example by using them as "blocking" antigenic peptides, activation of immunoregulatory cells, induction of an anti-TCR antibody or in mAb mediated deletion of the pathogenic V gene expressing T cells. Fragments consisting of amino acids homologous to the unique TCR sequence could be administered to a patient directly. Such sequences would act by blocking the TCR of the T cells making the T cells unable to attack the antigens of the patient. The specific peptides to be used in such a method would be homologous to the amino acid sequence of Vβ17seq1, Vβ17seq2, Vβ17seq3 or Vβ17seq4. More specifically, a peptide homologous to the sequence IGQ_N could also be used.

In an alternative method of immunotherapy, mAb could be produced, by conventional methods known in the art, which is directed to the unique TCR sequences. These mAb directed to the unique TCR sequences would target the unique TCR sequences which are believed to be pathogenic.

Specific monoclonal antibodies to be used in such a method would include mAb which recognize the CDR3 sequences of vβseq1, Vβseq2, Vβseq3 or Vβ17seq4 or portions thereof. A mAb directed to IGQ_N would also be useful.

Either the peptides or the mAb could be administered to an RA patient, for example in his synovial fluid, systemically, or orally, in a suitable pharmaceutical carrier.

EXAMPLE 1

In order to directly evaluate TCR V gene usage in the RA T cell repertoire, a panel of monoclonal antibodies specific for human TCR Vβ gene products was utilized. Control subjects included 25 healthy volunteers (female/male=2.4, mean age=43.3). Disease controls included patients with systemic lupus erythematosus (female/male=10.0; mean age=40) or 19 patients with non-RA inflammatory arthritis, including osteoarthritis, gout, Reiter's syndrome and monoarticular arthritis; (female/male=2.0; mean age=59.5). RA patients were defined using American Rheumatism Association criteria (Arnett et al., 1988, *Arthritis Rheum.*, 31:315–324). Patients were not selected with respect to medical therapy, which included aspirin, nonsteroidal anti-inflammatory drugs, corticosteroids, methotrexate, gold, hydroxychloroquine, or sulfasalazine. Serum samples from RA patients were assayed by latex fixation to determine if the patients were seropositive for RF. PB mononuclear cells (MNC) from some subjects were characterized for HLA DR haplotype using standard serologic reagents.

Peripheral blood samples were obtained by venipuncture, and SF samples were obtained at the time of therapeutic arthrocentesis. ST specimens were obtained from the Department of Pathology at The Hospital for Special Surgery following therapeutic arthroscopic synovectomy, open synovectomy, or total joint replacement. Synovial tissue was minced under sterile conditions and incubated in 20 ml. of an enzyme preparation containing RPMI 1640 (GIBCO Laboratories, Grand Island, N.Y.), 20% fetal calf serum (Whittaker Bioproducts, Inc., Walkersville, Md.), 1% penicillin and streptomycin, 1% glutamine (GIBCO), 0.5 mg/ml collagenase, 0.15 mg/ml DNase, and 0.1 mg/ml hyaluronidase (Sigma Chemical Co., St. Louis, Mo.) at 37° C., 5% $CO_2$ for 2–4 hours. Tissue was then mechanically disrupted using forceps and scalpel and pressed through a mesh sieve.

MNC were isolated from PB, SF, or ST digest on a Ficoll-Hypaque (Pharmacia, Uppsala, Sweden) gradient. In some cases, T cells were selectively enriched by resetting of MNC with sheep red blood cells (SRBC) followed by incubation at 4° C. for 16 hours and subsequent fractionation of rosetted and unrosetted cells over Ficoll-Hypaque.

The T cells were stained with the following monoclonal antibodies: OKT3 (anti-CD3, panT); OKT4 (anti-CD4, helper/inducer subset); OKT8 (anti-CD8, suppressor/cytotoxic subset, American Type Culture Collection, Rockville, Md.); βV3 (reactive with TCR Vβ3, T Cell Diagnostics, Cambridge, Mass.); C37 (reactive with TCR Vβ5.2/5.3, Wang et al., *Hybridoma*, 1986, 5:179); OT145 (reactive with TCR Vβ6.7a, Li et al., *J. Exp. Med.*, 1990, 171:221); 16G8 (reactive with TCR Vβ8, T Cell Diagnostics) S511 (reactive with TCR Vβ12, Bigler et al., *J. Exp. Med.*, 1983, 158:1000; C1 (reactive with TCR Vβ17, Freedman et al., *J. Exp. Med.*, 1991, 174:891) and F1 (reactive with TCR Vα2.3, Janson et al., *Cancer Immunol. Immunother.*, 1989, 28:225).

$1-2\times10^5$ MNC or T cells were incubated with buffer alone or a saturating concentration of mAb at 4° C. for 30 minutes. Cells were then washed three times and incubated with a saturating concentration of fluorescein-labeled $F(ab')_2$ fragments of goat anti-mouse IgG (Tago, Inc., Burlingame, Calif.) at 4° C. for 30 minutes. After 3 washes in buffer, the cells were analyzed on a cytofluorograph. In some cases, two color immunofluorescence analysis was performed. The above procedure was followed by a blocking step, with cells incubated at 4° C. for 30 minutes with an irrelevant murine mAb (anti-trinitrophenol). After three washes, the cells were incubated with a phycoerythrin-labeled murine mAb, washed, and prepared for analysis on a cytofluorograph. Cell fluoroscence was analyzed on an Ortho IIs cytofluorograph, gating on the small, nongranular lymphocyte population. The percentage of cells fluorescent with buffer or irrelevant control murine mAb and fluorescein-labeled goat anti-mouse IgG alone was subtracted. Cytofluorograph histograms of cells stained with anti-TCR mAb exhibited a peak of fluorescence distinct from the negative peak and with fluorescence intensity approximating that of cells stained with anti-CD3 mAb.

EXAMPLE 2

PB MNC from healthy subjects and from patients with seropositive RA, non-RA inflammatory arthritis, or SLE were isolated and the percentage of CD3-positive cells expressing the TCR Vβ gene product identified by a panel of anti-TCR mAb determined by indirect immunofluoresence analysis. The mean percentage of T cells reactive with mAb C37 (Vβ 5.2, 5.3), OT145 (Vβ 6.7a), 16G8 (Vβ 8), or S511 (Vβ 12) is similar in each of the groups tested (Table 1), a result consistent with previous studies of T cell repertoire in autoimmune disease which used these monoclonal reagents (Posnett et al, *J. Immunol.*, 1988, 141:1963; Gudmundsson et al., *Scand. J. Immunol.*, 1992, 36:681). In contrast, analysis of CD3-positive PB cells reactive with the more recently available mAb C1, specific for the Vβ 17 TCR gene product, demonstrates a significant increase in the mean percentage of Vβ 17-positive cells in RA patients when compared with the normal subjects or control patients (p=0.002) (Table 1 and FIG. 1). No significant increase in Vβ 17-positive cells is observed in the non-RA arthritis or SLE patients when compared with the normal controls. Taken together, these results demonstrate a selective expansion of Vβ 17-positive T cells in the PB of RA patients.

TABLE 1

Summary of T Cell Phenotypes of RA and Control Subjects
% of CD3-Positive Cells*

| T Cell Antigen:<br>(Monoclonal Antibody) | CD4<br>(OKT4) | CD8<br>(OKT8) | IL-2R p55<br>(Anti-Tac) | Vβ.2/5.3<br>(C37) | Vβ6.7a<br>(OT145) | Vβ8<br>(16G8) | Vβ12<br>(S511) | Vβ17<br>(C1) |
|---|---|---|---|---|---|---|---|---|
| Peripheral Blood | | | | | | | | |
| Normal Subjects | 71.0 ± 8.9(14) | 30.4 ± 11.3(14) | 4.5 ± 2.9(14) | 2.7 ± 1.7(15) | 3.6 ± 2.1(21) | 3.8 ± 2.1(6) | 2.0 ± 0.9(20) | 4.7** ± 1.3(21) |
| SLE | 54.5 ± 11.8(13) | 42.1 ± 14.1(13) | 6.8 ± 8.0(13) | 2.9 ± 1.4(11) | 3.2 ± 1.6(25) | 3.7 ± 1.2(12) | 2.3 ± 1.7(21) | 4.9** ± 1.2(25) |
| Non-RA Arthritis | 54.9 ± 14.7(7) | 41.4 ± 16.8(8) | 12.6 ± 19.2(7) | 3.5 ± 1.8(7) | 3.1 ± 1.6(7) | 10.7 ± 9.3(4) | 2.3 ± 0.6(7) | 4.3** ± 1.6(7) |
| RA | 70.1 ± 19.3(27) | 37.0 ± 18.7(27) | 8.9 ± 7.7(27) | 3.4 ± 1.8(22) | 3.2* ± 2.5(28) | 5.1 ± 3.3(18) | 2.4 ± 1.9(29) | 6.5* ± 2.7(28) |
| Synovial Fluid | | | | | | | | |
| Non-RA Arthritis | 6.24 ± 18.6(15) | 31.3 ± 14.1(15) | 9.5 ± 4.4(15) | 3.1 ± 1.9(17) | 3.6 ± 2.1(17) | 4.3 ± 4.4(12) | 3.9 ± 4.2(15) | 5.3** ± 2.0(19) |
| RA | 53.9 ± 16.8(46) | 48.7 ± 13.0(45) | 12.3 ± 6.6(45) | 3.8 ± 2.1(45) | 3.7 ± 2.4(48) | 3.9 ± 2.2(32) | 3.4 ± 3.8(47) | 8.5** ± 4.1(49) |
| Synovial Tissue | | | | | | | | |
| RA | 63.2 ± 15.2(19) | 41.6 ± 23.1(19) | 9.7 ± 7.0(20) | 2.6 ± 2.2(17) | 3.8 ± 2.7(21) | 4.1 ± 2.5(15) | 3.3 ± 4.5(19) | 6.7 ± 2.2(21) |

*Isolated T cells were analyzed by indirect immunofluroescence on a cytoflurograph. The percentage of CD-3 positive cells expressing each T cell surface antigen was determined. Shown are the means ± standard deviation and the number of individuals analyzed ( ) for each subject group studied.
**p = 0.002
***p = 0.001

EXAMPLE 3

To characterize the T cell repertoire at the site of pathology in patients with RA, the synovial fluid, SF T cells were isolated from 49 patients with seropositive RA and analyzed for TCR Vβ gene usage by indirect immunofluoresence staining (Table 1 and FIGS. 1A and 1B). The mean percentage of CD3-positive cells reactive with the Vβ 17-specific mAb C1 is significantly elevated (p=0.001) in the RA patients (8.5%+4.1) when compared with the percentage Vβ 17-positive cells in the 19 SF specimens from patients with non-RA inflammatory arthritis (5.3%+2.0). Strikingly, 31% (15/49) of the RA fluid samples and 0/19 of the control samples contain greater than 10% Vβ 17-positive T cells (FIGS. 1A and 1B). In contrast, no significant differences were noted between RA and control SF in the percentages of Vβ 5.2/5.3, Vβ 6.7a, Vβ 8, or Vβ 12-positive T cells.

Figure 2:
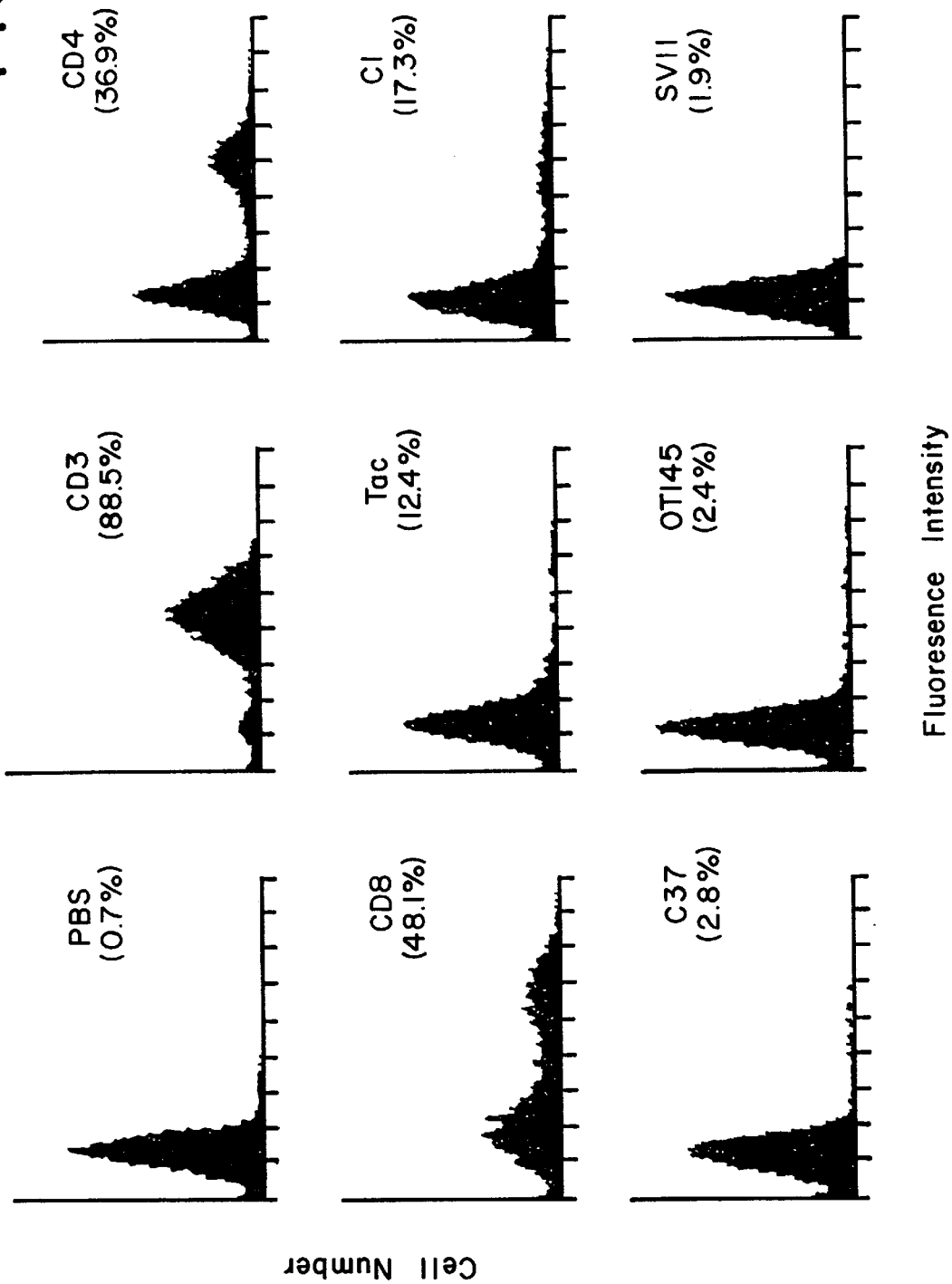
FIG. 2 depicts MNC isolated from synovial fluid and analyzed by indirect immunofluorescence for expressionof the T cell surface epitopes indicated. Fluorescence is demonstrated on the abscissa (log scale) and cell number on the ordinate (linear scale) of each cytofluorograph histogram.

A representative study of SF T cells from an RA patient with an elevated percentage of Vβ 17-positive T cells is presented in FIG. 2. Analysis of the TCR repertoire in this patient shows 17.3% of cells expressing the Vβ 17 gene product, but only 2.8%, 2.4%, and 1.9% expressing the Vβ 5.2/5.3, Vβ 6.7a, and Vβ 12 products, respectively. Thus, of the five TCR Vβ gene families studied, only Vβ 17 is significantly increased in expression at the site of disease in the RA patients. While we do not have HLA typing data on all of our subjects, an increased percentage of Vβ 17-positive T cells in RA SF does not appear to correlate directly with expression of the DR4 RA susceptibility allele in these patients. To date, 4 of the 15 patients with >10% Vβ 17-positive SF T cells have been HLA typed, and their DR haplotypes are: DR 4,7; DR2,3; DRw13; and DR5,7.

EXAMPLE 4

Figure 3A:
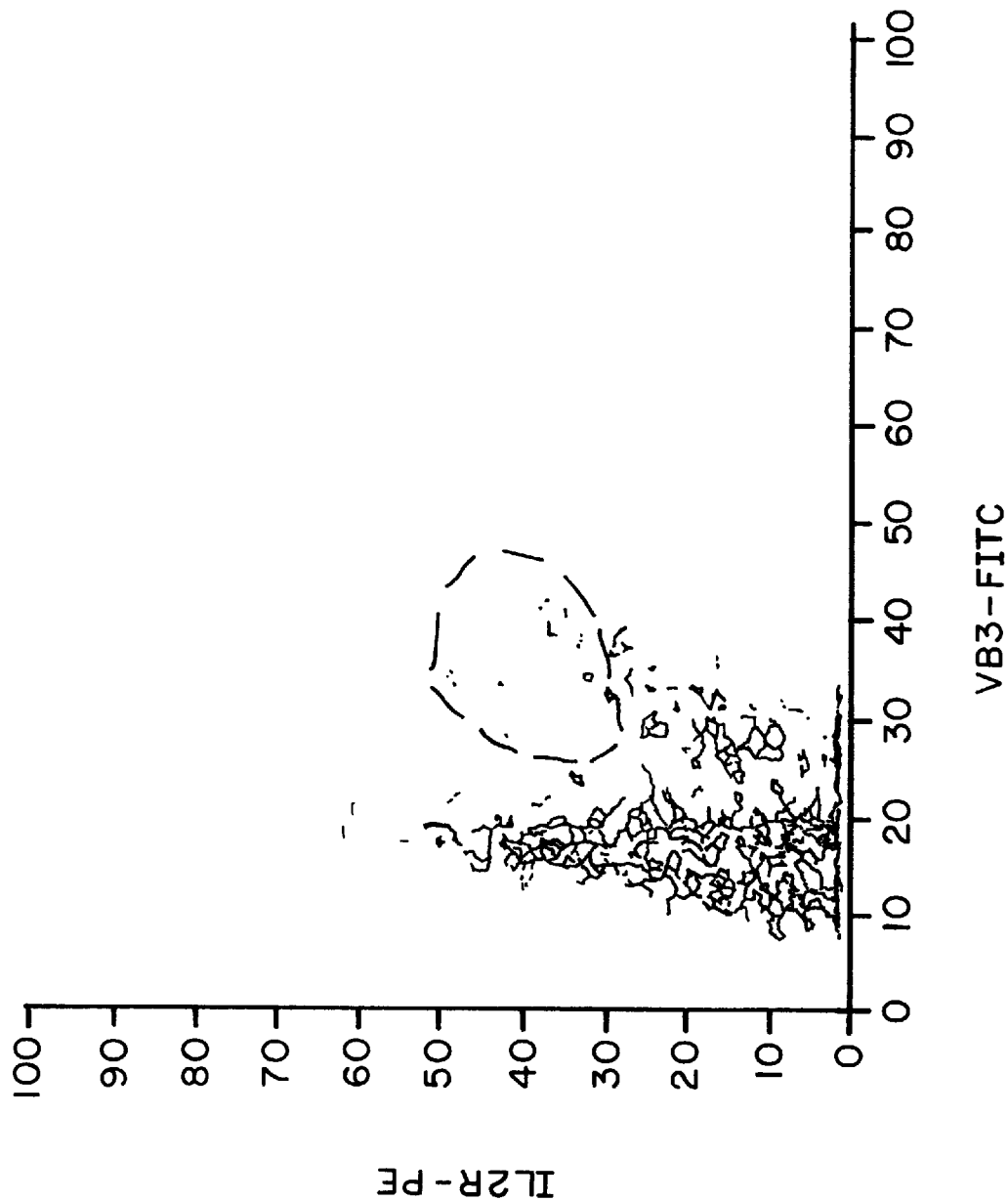
FIGS. 3A and 3B depicts two color immunofluorescence analysis of SF T cells. SF T cells were stained with anti-Vβ (FIG. 3A) or anti-Vβ 17 (FIG. 3B) mAb.
Figure 3B:
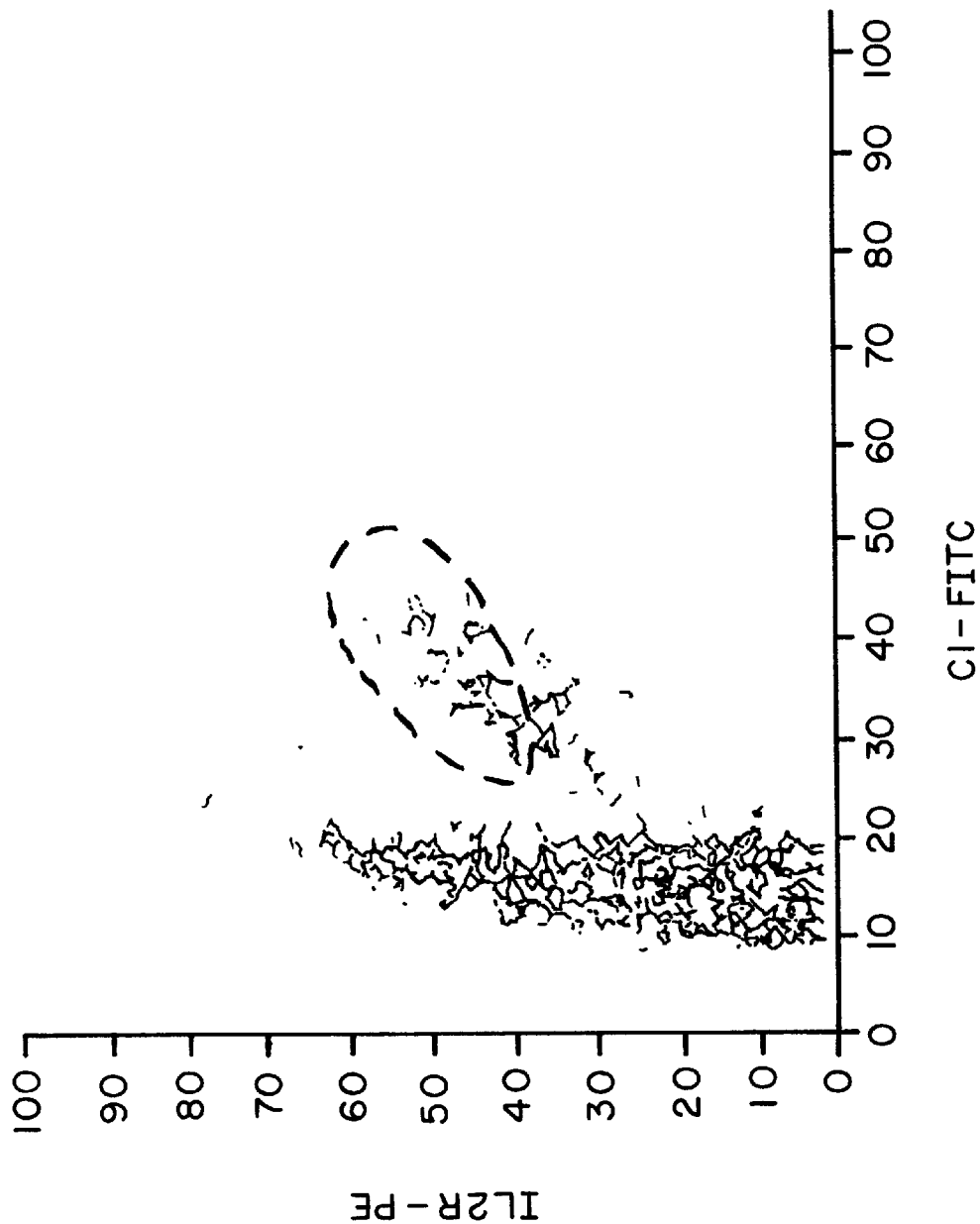

Two color immunofluorescence analysis was performed on 5 RA SF samples and on 3 non-RA inflammatory arthritis SF samples, all of which contained less than 10% Vβ 17-positive T cells (Table 2). Th SF cells were stained with anti-Vβ 3 or anti-Vβ 17 mAb and FITC-goat anti-mouse IgG, followed by phycoerythrin anti-IL-2 receptor antibody (anti-p55-TAC) and immunoflouresence was assessed on a cytofluorograph. The Tac-positive cells are found almost exclusively among the CD4-positive SF T cells from the RA patients. Moreover, Tac-positive T cells were enriched among the Vβ 17-positive T cells from the RA SF, but not from the non-RA arthritis SF. Cytofluorograph histograms demonstrating Tac expression on a high proportion of Vβ 17-positive T cells (approximately 45%), but not Vβ 3-positive T cells (less than 10%), from an RA SF specimen are shown in FIG. 3. Thus, even RA SF that do not contain a markedly expanded Vβ 17-positive T cell population show evidence for preferential activation of that T cell fraction, when compared with T cells expressing other Vβ gene products.

EXAMPLE 5

In order to assess the pathogenic potential of Vβ17+ synovial tissue T cells, an informative RA patient was analyzed. This patient has "classic" rheumatoid factor-positive (RF+) polyarticular, symmetrical joint inflammation, expresses the RA associated MHC class II antigen DR4 and exhibits an expanded Vβ17+T cell population. Over an eighteen month period of study, this patient maintained a skewed peripheral blood T cell repertoire characterized by persistently elevated percentages of Vβ17+T cells, i.e. 13.2–15.7% as compared to an average normal value of 5.3%.

After the 18 month period, synovial tissue was explanted from the patient by an arthroscopic synovectomy and the synovial T cells were isolated to use in: 1) analysis of cell surface antigen expression; 2) molecular characterization of α/B TCR rearrangements; and 3) in vitro propagation and cloning of Vβ17+ T cell clones.

In order to analyze the cell surface antigen expression, synovial tissue T cells were washed in phosphate-buffered saline (PBS) and stained with a panel of monoclonal antibodies as described in Example 1. T cells were incubated with buffer alone or a saturating concentration of mAb at 4° C. for 30 minutes, washed three times with PBS, and incubated with a saturating concentration of flurescein-labeled F(ab')$_2$ fragments of goat anti-mouse IgG (Tago, Inc., Burlingname, Calif.) at 4° C. for 30 minutes. After 3 washes in PBS, the cells were analyzed on a cytoflurograph. Two color immunofluorescence analysis were performed using phycoerythrin-labeled anti-CD4 and anti-CD8 mAb obtained from Coulter Immunology (Hialeah, Fla.). The above procedure was followed by a blocking step, with cells incubated at 4° C. for 30 minutes with an irrelevant murine mAb (anti-trinitrophenol). After three washes, the cells were incubated with a phycoerythrin-labeled murine mAb, washed, and analyzed on an Ortho IIs cytofluorograph, gating on the small, nongranular lymphocyte population. The percentage of cells fluorescent with buffer or irrelevant control murine mAb and flurescein-labeled goat anti-mouse IgG alone was subtracted. The results are shown in Table 3.

TABLE 2

Distribution of Tac-Positive Cells Among Synovial Fluid T Cell Subpopulations & of Total Tac+ In T Cell Population*

| T Cell Population | RA Synovial Fluids | | | | Non-RA Arthritis Synovial Fluids | | | |
|---|---|---|---|---|---|---|---|---|
| CD4 | 79.3 | 80.0 | 81.6 | 100 | 90.3 | 86.2 | 59.3 | 70.7 |
| CD8 | 3.4 | 10.0 | 18.4 | 0 | 11.1 | 50.8 | 14.8 | 27.6 |
| Vβ3 | 0 | 4.3 | N.D. | 3.4 | N.D. | N.D. | N.D. | N.D. |
| Vβ5.2, 5.3 | 3.4 | 8.7 | 6.8 | 4.8 | 6.6 | 3.1 | 3.7 | 3.4 |
| Vβ6.7a | 6.9 | 4.3 | 1.9 | 10.9 | 13.1 | 6.9 | 11.1 | 3.4 |
| Vβ12 | 5.2 | 3.4 | 4.3 | 3.9 | 6.8 | 8.2 | 4.6 | 3.7 |
| Vβ17 | 48.3 | 21.7 | 10.7 | 18.4 | 18.0 | 4.6 | 3.7 | 3.4 |

*Two color immunofluorescence analysis was performed on RA or non-RA SF T cells using phycoerythrin-labeled anti-IL-2 receptor mAb and either anti-CD4, anti-CD8, or anti-TCR Vβ mAb followed by FITC-labeled goat anti-mouse IgG. The distribution of the total Tac-positive T cells between CD4 and CD8 subsets, and among the 5 TCR Vβ populations tested, was calculated by determining the % of cells positive with both anti-IL-2 receptor and anti-T cell mAb/the % of IL-2 receptor- positive cells.

TABLE 3

|  | CD4 | CD8 | Vβ3 | Vβ5.2/3 | Vβ6.7a | Vβ8 | Vβ12 | Vβ17 |
|---|---|---|---|---|---|---|---|---|
| % mAb⁺ T cells | 72.3 | 29.2 | 4.8 | 2.6 | 1.5 | 1.6 | 3.2 | 7.9 |
| % mAb⁺ T cells which are CD4⁺ | 100 | 0 | 30 | 31 | 10 | 50 | 50 | 89 |

As shown in the table, the distribution of Vβ17⁺ T cells in this patient's peripheral blood reflected the overall CD4/CD8 ratio (¼), however, synovial tissue TCR repertoire analysis with mAbs demonstrated relative abundance of Vβ17⁺ T cells and their selective presentation in the CD4⁺ subset.

EXAMPLE 6

In order to assess oligoclonality of Vβ17⁺ T cells at the side of pathology of RA, sequences of the highly polymorphic antigen binding CDR3 region in the Vβ17 transcripts were examined. The Vβ17 transcripts were derived from the synovial tissue and peripheral blood of the RA patient described in Example 5. These transcripts were analyzed using reverse transcriptese-polymerase chain reaction (RT-PCR) with total cellular RNA as a template.

Total cellular RNAs were isolated from the peripheral blood or synovial tissue T cells by the guanidinium/cesium chloride centrifugation method or an acidified guanidinium/phenol/chloroform method as described in the manual of (RNazol™, TEL-TEST, INC., Texas. The first-strand cDNAs were reverse transcribed with cDNA synthesis kit (cDNA Cycle Kit, Invitrogen, San Diego, Calif.). TCR Vβ gene segments were amplified by polymerase chain reaction (PCR) with the 5' sense oligonucleotide primers specific for Vβ17 (5'-ACAGCGTCTCTCGGGAGA-3') (seq. I.D. No. 15), Vβ6.7 (5'-AGGCAACAGTGCACCAGAC-3') (seq. I.D. No. 16), Vβ1 (5'GCACAACAGTTTCCCTGACTT-3') (seq. I.D. No. 17), in connection with a antisense primer complementary to TCR β constant region sequence (5'-GGGTGTGGGAGATCTCTGCT-3') (seq. I.D. No. 18). The PCR products were subcloned into a T/A cloning vector according to the instruction manual provided by Invitrogen, San Diego, Calif. The ligation mixture was used to transform competent DH5α cells. The plasmid DNA samples were prepared and subject to sequencing using a sequencing kit (Sequenase version 2.0, United States Biochemical, Ohio).

A total of twenty-nine (29) Vβ17 cDNA clones from synovial tissue T cells were sequenced. Twelve (12) of the twenty-nine (29) clones contain the identical sequence. Eleven (11) of the twenty-nine (29) clones contain a distinct but structurally-related sequence. The two dominant synovial tissue sequences are designated Vβ17seq1 and Vβ17seq2, respectively. The nucleotide and deduced amino acid sequences in CDR3 region are shown in FIG. 4. Comparison of these sequences reveals identity in length as well as conservation of several amino acids with the CDR3 region, including isoleucine (I) at position #95 and asparagine at position #99.

In contrast, Vβ17 transcripts from the RA patients peripheral blood were heterogeneous. Twenty-eight cDNA clones were sequenced and twenty-two distinct patterns of CDR3 sequences is were present. None of the peripheral blood cDNA clones contained the dominant synovial tissue Vβ17 sequences.

EXAMPLE 7

Rearrangements of Vβ6.7a and Vβ1 gene subfamilies were also assessed in order to ensure that the clonal dominance of the synovial RNA samples of Example 6 were not an aspect of the PCR amplification.

As shown in Table 3, Vβ6.7a⁺ T cells represent only 1.5of synovial T-cells, 6 distinct rearrangements were observed in the 8 clones sequenced. Three distinct rearrangements in 9 Vβ1 T cell clones sequenced were found. These rearrangements were totally heterogeneous with respect to CDR3 sequences and the JB segment usage.

The results described in this Example, along with the previous examples, demonstrate that Vβ17⁺ T cells express structurally related CDR3 sequences are selectively expanded in the synovial tissue of RA patients.

EXAMPLE 8

In order to examine the possible role played by T cells expressing these dominant Vβ17 sequences in the rheumatoid process, synovial tissue T cells were isolated and expanded in vitro. Synovial tissue cells were incubated at 1×10⁶/ml in RPMI 1640, 10% fetal calf serum, 1% penicillin and streptomycin, 1% glutamine (culture medium) containing Vβ17 selective microbial superantigen *Mycoplasma arthritidis* mitogen (MAM, from Dr. B. Cole, University of Utah School of Medicine, Salt Lake City, Utah) at a final concentration of 1/2000, or 10 μg/ml of anti-Vβ17 mAb C1.

As described in Friedman et al., *J. Exp. Med.* 174, 891 (1991), after 4 days of culture at 37° C., purified interleukin 2 (IL-2) (Schiapparelli, Columbia, Md.) was added to each culture at a final concentration of 10%. TCL were further expanded by the weekly addition of x-irradiated sodium periodate-treated allogeneic peripheral blood non-T cells and IL-2.

While a large number of distinct Vβ17 TCR sequences are represented among the bulk T cell lines (TCLs) generated, two Vβ17 transcripts from 1 TCL, designated culture 5, were analyzed using the method of Example 6. As shown in FIG. 4, the first transcript from culture 5, termed Vβ17seq3, utilizes Vβ17-Dβ2-Jβ2.1-Cβ2. This sequence is highly homologous to the dominant synovial tissue sequences, Vβ17seq1 and Vβ17seq2.

The second Vβ17 transcript from culture 5, Vβ17seq4, shares the amino acid residue "I" at position #95 and "N" at position #99 with Vβ17seq1, 2, and 3 (FIG. 4).

EXAMPLE 9

α chain usage by the culture 5-derived T cell clones expressing Vβ17seq3 and 4 was analyzed. The Culture 5 TCL cells were cloned by limited dilution using $5 \times 10^4$ x-irradiated periodate-treated allogeneic feeder cells and IL-2, then further expanded with epriodate-treated feeder cells and IL-2.

TCR α rearrangements were analyzed using PCR and a panel of Vα specific primers from a TCR α constant region primer, (J. R. Oksenberg et al., *Nature* 345: 344 (1990)), except primers for the Vα2 subfamily and for the TCR α chain constant region sequence. The sense oligonucleotide primer for Vα2, 5'AGGTCGACGAATGATGAAATCCTTGAGAG-3' (seq. I.D. No. 19), is located at the 5' leader of Vα2 coding sequence and contains a Sal I site inside for further subcloning. The 3' antisense oligonucleotide complementary to TCR α constant region sequence is 5'-AATAGGTCGACAGACTTGTCACTGG-3' (seq. I.D. No. 20) in which two nucleotides have been changed to create a Sal I site for future subcloning purpose.

This analysis revealed expression of only Vα2.3 by T cell clone expressing Vβ17seq3. Formal sequencing was performed and yielded a sequence consisting of Vα2.3-Jα (IGRJa09)-Cα (FIG. 5). This Vα designation is consistent with positive staining of this T cell clone by the Vα2.3 specific mAb F1 (Janson et al., 1989, *Cancer Immunol. Immunother.* 28: 225). A similar analysis of T cells expressing the Vβ17seq4 has yield a TCR α rearrangement of Vα3.1-Jα-Cα (FIG. 5). Thus, both TCR α and β chain of T cell clones expressing receptors homologous to the dominant synovial tissue Vβ17 transcripts have been characterized.

EXAMPLE 10

Figure 6A:
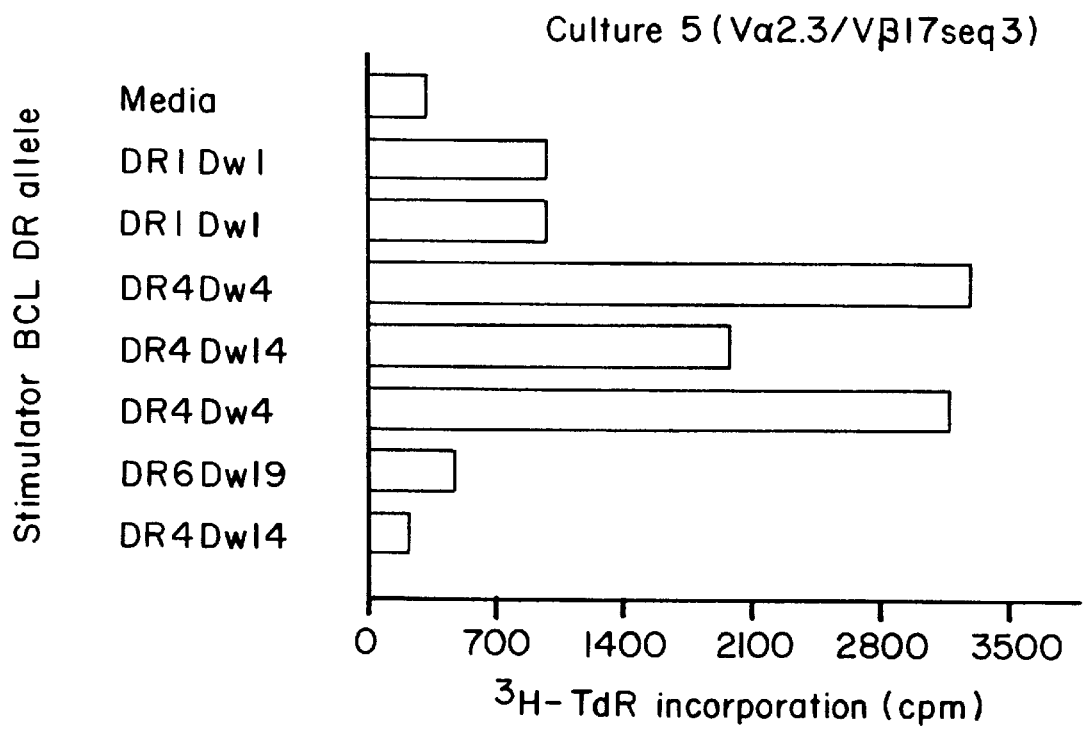
FIGS. 6A and 6D show the proliferation of synovial tissue T cell clones induced by EBV-transformed B cell lines.
Figure 6B:
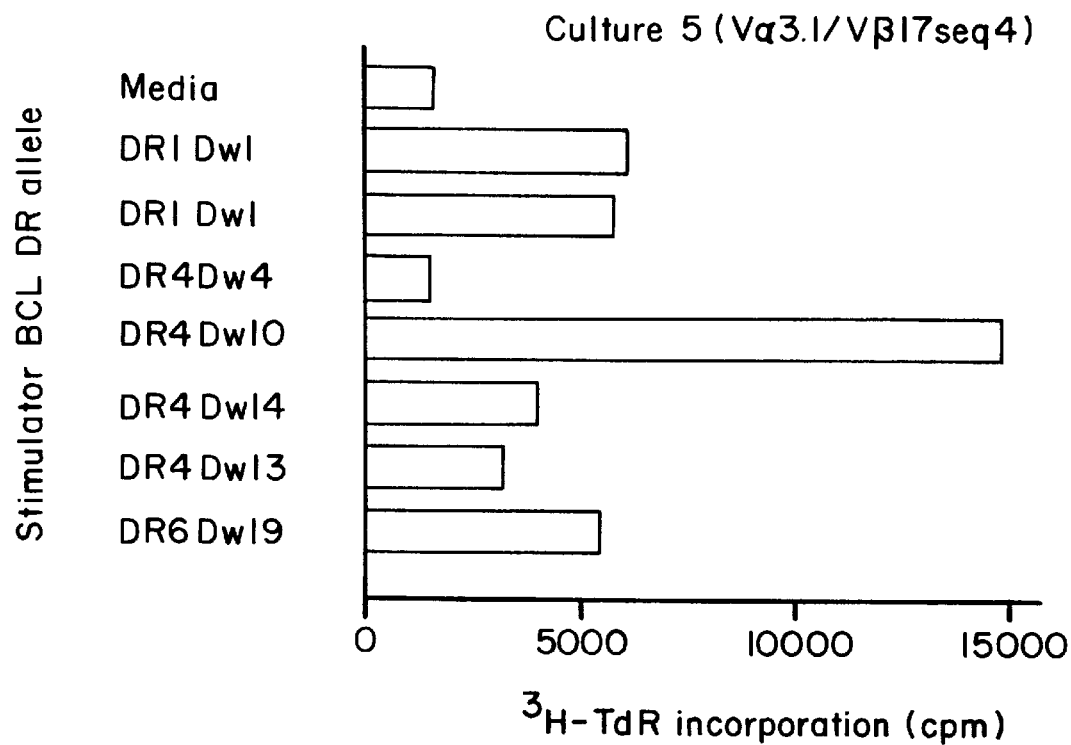
Figure 6C:
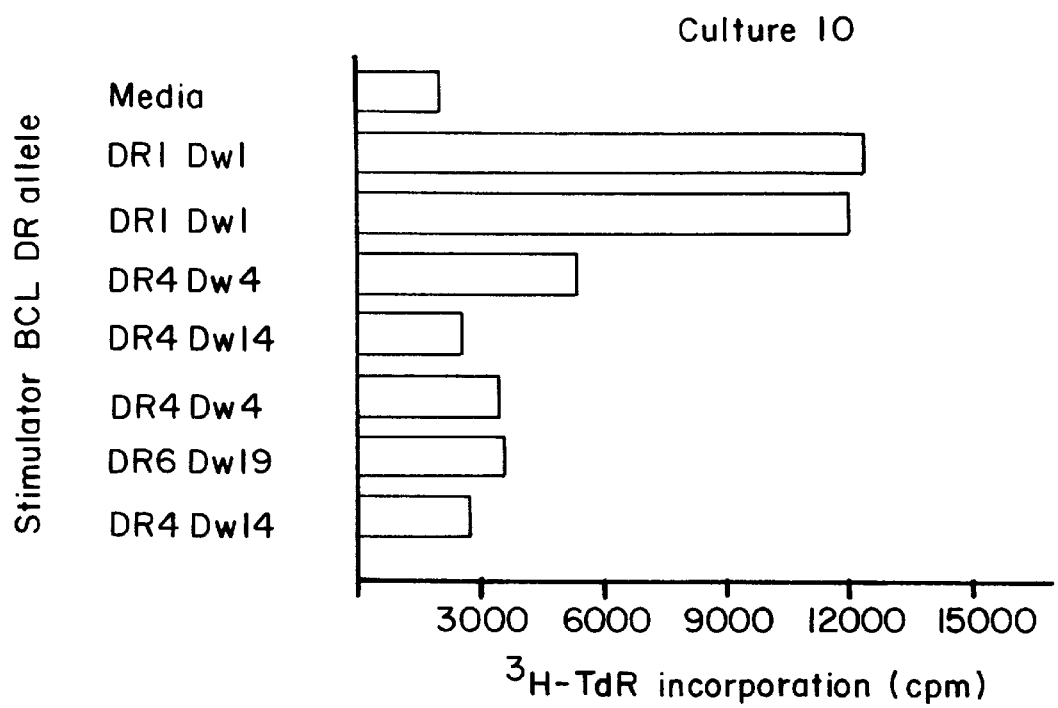
Figure 6D:
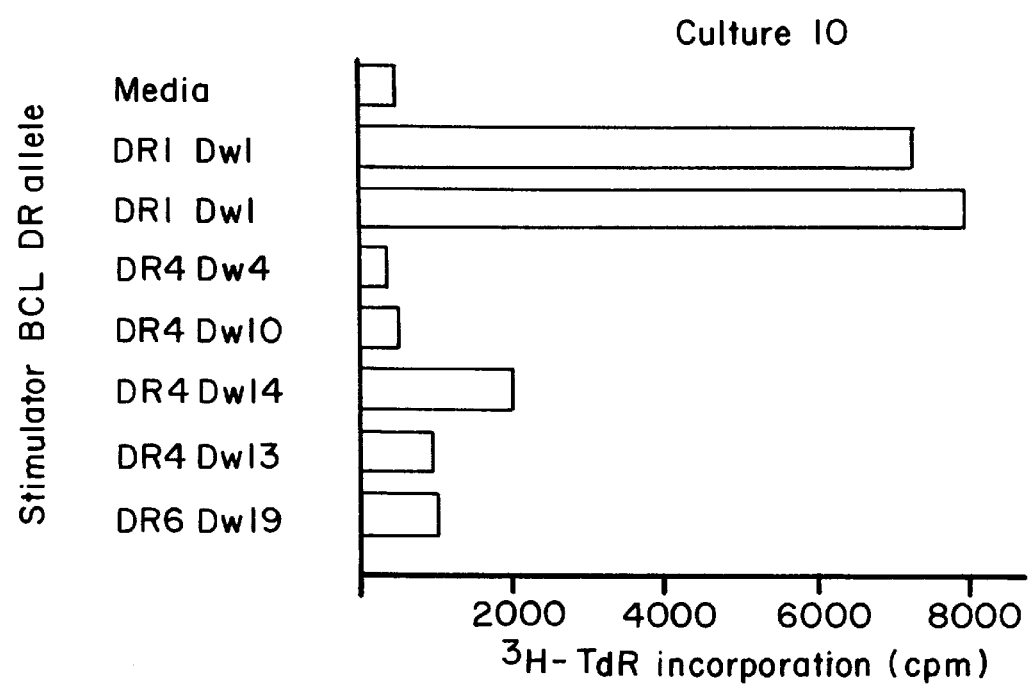

The culture 5 derived T cell clones were assayed for proliferative response against a panel of Epstein-Barr virus (EBV) transformed DR homozygous lymphoblastoid B cell lines (BCL). As a control, an uncloned synovial tissue Vβ17$^+$, CD4$^+$ T cell line designated culture 10 was assayed simultaneously (FIGS. 6A–6D). $2 \times 10^4$ T cell line cells were cultured, in triplicate, in 96 well round-bottom tissue cultures plates with medium alone or with $5 \times 10^4$ EBV-transformed HLA DR homozygous B cell line cells (from Dr. S. Y. Yang, Sloan Kettering Institute, New York, N.Y.) x-irradiated with 4000 rads from a Cesium source. Cultures were supplemented with 5% IL-2 and after 96 hours, 2 µCi $^3$[H]-thymidine added to each culture and 16 hours later, the cultures were transferred to filter paper using an automated cell harvester and counted in a beta counter. Clones expressing Vα2.3/Vβ17seq3 showed poor growth characteristics and low levels of proliferation in response to all stimuli, including superantigens and anti-TCR mAb. However, as shown in the FIG. 6A and FIG. 6C, these cells proliferate selectively to BCL cells expressing RA associated alleles of DR4, Dw4 and Dw14. T cells expressing Vα3.1/Vβ17seq4 are highly responsive to DR4, Dw10 bearing BCL cells (FIGS. 6B9 and 6D). This preliminary evidence of DR4 recognition by synovial T cells expressing the conserved CDR3 sequences is intriguing. It is not clear, however, if these clones recognize as yet undefined antigenic peptides in association with alleles of this MHC class II antigen or are specific for the DR4 alleles themselves.

What is claimed:

1. An isolated T cell receptor polypeptide comprising an amino acid sequence selected from the group consisting of IGQ-N, (SEQ ID NO. 13), IQG-N (SEQ ID NO: 22) and IQNP (SEQ ID NO: 23).

2. The isolated T cell receptor polypeptide of claim 1, comprising a Vβ CDR3 Vβ17seq1 amino acid sequence, as set forth in FIG. 4, SEQ ID NO:1.

3. The isolated T cell receptor polypeptide of claim 1, comprising a Vβ CDR3 Vβ17seq2 amino acid sequence, as set forth in FIG. 4, SEQ ID NO:3.

4. The isolated T cell receptor polypeptide of claim 1, comprising a Vβ CDR3 Vβ17seq3 amino acid sequence, as set forth in FIG. 4, SEQ ID NO:5.

5. The isolated T cell receptor polypeptide of claim 1, comprising a Vα CDR3 Vα2.3-Jα(IGRJa09)-Cα amino acid sequence, as set forth in FIG. 5, SEQ ID NO:9.

6. The isolated T cell receptor polypeptide of claim 1, comprising a Vα CDR3 Vα3.1-Jαk-Cα amino acid sequence, as set forth in FIG. 5, SEQ ID NO: 11.

7. An isolated T cell receptor polypeptide comprising a Vβ CDR3 Vβ17seq4 amino acid sequence, as set forth in FIG. 4, SEQ ID NO:7.

\* \* \* \* \*

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: peptide (v) FRAGMENT TYPE: internal (vi) ORIGINAL SOURCE:
      (A) ORGANISM: Homo sapiens (vii) IMMEDIATE SOURCE:
      (B) CLONE: vb17 seq 1-aa (xi) SEQUENCE DESCRIPTION: SEQ ID NO:1:

```
Cys Ala Ser Ser Ile Gly Gln Glu Asn Tyr Glu Gln Tyr Phe Gly Pro
1               5                   10                  15

Gly Thr Arg Leu Thr Val Thr
            20
```

(2) INFORMATION FOR SEQ ID NO:2:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
        (A) ORGANISM: Homo sapiens (vii) IMMEDIATE SOURCE:
        (B) CLONE: Vb17-seq 1-nt (xi) SEQUENCE DESCRIPTION: SEQ ID NO:2:

```
TGTGCCAGTA GTATTGGTCA GGAGAACTAC GAGCAGTACT TCGGGCCGGG CACCAGGCTC    60

ACGGTCACA                                                            69
```

(2) INFORMATION FOR SEQ ID NO:3:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Homo sapiens (vii) IMMEDIATE SOURCE:
        (B) CLONE: vb17-seq2-aa (xi) SEQUENCE DESCRIPTION: SEQ ID NO:3:

```
Cys Ala Ser Ser Ile Gln Gly Tyr Asn Glu Gln Phe Phe Gly Pro Gly
1               5                   10                  15

Thr Arg Leu Thr Val Leu
            20
```

(2) INFORMATION FOR SEQ ID NO:4:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
        (A) ORGANISM: Homo sapiens (vii) IMMEDIATE SOURCE:
        (B) CLONE: vb17-seq2-nt (xi) SEQUENCE DESCRIPTION: SEQ ID NO:4:

```
TGTGCCAGTA GTATACAGGG GTACAATGAG CAGTTCTTCG GGCCAGGGAC ACGGCTCACC    60

GTGCTA                                                              66
```

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Homo sapiens (vii) IMMEDIATE SOURCE:
        (B) CLONE: vb17-seq3-aa (xi) SEQUENCE DESCRIPTION: SEQ ID NO:5:

```
Cys Ala Ser Ser Ile Gly Gln Thr Asn Glu Gln Phe Phe Gly Pro Gly
1               5                   10                  15

Thr Arg Leu Thr Val Leu
            20
```

(2) INFORMATION FOR SEQ ID NO:6:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
        (A) ORGANISM: Homo sapiens (vii) IMMEDIATE SOURCE:
        (B) CLONE: vb17-seq3-nt (xi) SEQUENCE DESCRIPTION: SEQ ID NO:6:

```
TGTGCCAGTA GTATCGGGCA GACGAATGAG CAGTTCTTCG GGCCAGGGAC ACGGCTCACC    60

GTGCTA                                                              66
```

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Homo sapiens (vii) IMMEDIATE SOURCE:
        (B) CLONE: vb17-seq4-aa (xi) SEQUENCE DESCRIPTION: SEQ ID NO:7:

```
Cys Ala Ser Ser Ile Pro Arg Ala Asn Glu Gln Phe Phe Gly Pro Gly
```

```
1               5                   10                  15
Thr Arg Leu Thr Val Leu
            20
```

(2) INFORMATION FOR SEQ ID NO:8:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
        (A) ORGANISM: Homo sapiens (vii) IMMEDIATE SOURCE:
        (B) CLONE: vb17-seq4-nt (xi) SEQUENCE DESCRIPTION: SEQ ID NO:8:

```
TGTGCCAGTA GTATACCCCG GGCCAATGAG CAGTTCTTCG GGCCAGGGAC ACGGCTCACG        60

GTGCTA                                                                  66
```

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Homo sapiens (vii) IMMEDIATE SOURCE:
        (B) CLONE: Va2.3-aa (xi) SEQUENCE DESCRIPTION: SEQ ID NO:9:

```
Cys Val Val Lys Gly Gly Gly Asn Lys Leu Val Phe Gly Ala Gly Thr
1               5                   10                  15

Ile Leu Arg Val Lys Ser Tyr Ile Gln Asn Pro
            20                  25
```

(2) INFORMATION FOR SEQ ID NO:10:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
        (A) ORGANISM: Homo sapiens (vii) IMMEDIATE SOURCE:
        (B) CLONE: Va2.3-nt (xi) SEQUENCE DESCRIPTION: SEQ ID NO:10:

```
TGTGTGGTGA AGGGAGGGGG AAACAAGCTG GTCTTTGGCG CAGGAACCAT TCTGAGAGTC        60
```

AAGTCCTATA TCCAGAACCC T                                                        81

(2) INFORMATION FOR SEQ ID NO:11:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Homo sapiens (vii) IMMEDIATE SOURCE:
        (B) CLONE: Va3.1-aa (xi) SEQUENCE DESCRIPTION: SEQ ID NO:11:

Cys Ala Thr Leu Gly Gly Ser Asn Tyr Lys Leu Thr Phe Gly Lys Gly
1               5                   10                  15

Thr Leu Leu Thr Val Asn Pro Asn Ile Gln Asn Pro
            20                  25

(2) INFORMATION FOR SEQ ID NO:12:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
        (A) ORGANISM: Homo sapiens (vii) IMMEDIATE SOURCE:
        (B) CLONE: Va3.1-nt (xi) SEQUENCE DESCRIPTION: SEQ ID NO:12:

TGTGCTACAC TGGGAGGTAG CAACTATAAA CTGACATTTG GAAAAGGAAC TCTCTTAACC       60

GTGAATCCAA ATATCCAGAA CCCT                                             84

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Homo sapiens (vii) IMMEDIATE SOURCE:
        (B) CLONE: V-D junction (xi) SEQUENCE DESCRIPTION: SEQ ID NO:13:

Ile Gly Gln Xaa Asn
1               5

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Homo sapiens (vii) IMMEDIATE SOURCE:
        (B) CLONE: RA-DR peptide (xi) SEQUENCE DESCRIPTION: SEQ ID NO:14:

Gln Lys Arg Ala Ala
1            5

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
        (A) ORGANISM: Homo sapiens (vii) IMMEDIATE SOURCE:
        (B) CLONE: VB17-5'PRIMER (xi) SEQUENCE DESCRIPTION: SEQ ID NO:15:

ACAGCGTCTC TCGGGAGA                                      18

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
        (A) ORGANISM: Homo sapiens (vii) IMMEDIATE SOURCE:
        (B) CLONE: VB 6.7- 5' PRIMER (xi) SEQUENCE DESCRIPTION: SEQ ID NO:16:

AGGCAACAGT GCACCAGAC                                    19

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: NO (vi) ORIGINAL SOURCE:
         (A) ORGANISM: Homo sapiens (vii) IMMEDIATE SOURCE:
         (B) CLONE: Vb1- 5' PRIMER (xi) SEQUENCE DESCRIPTION: SEQ ID NO:17:

GCACAACAGT TTCCCTGACT T                                              21

(2) INFORMATION FOR SEQ ID NO:18:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA to mRNA (iv) ANTI-SENSE: YES (vi) ORIGINAL SOURCE:
         (A) ORGANISM: Homo sapiens (vii) IMMEDIATE SOURCE:
         (B) CLONE: TCR B -ANTISENSE (xi) SEQUENCE DESCRIPTION: SEQ ID NO:18:

GGGTGTGGGA GATCTCTGCT                                                20

(2) INFORMATION FOR SEQ ID NO:19:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: cDNA to mRNA (iv) ANTI-SENSE: NO (vi) ORIGINAL SOURCE:
         (A) ORGANISM: Homo sapiens (vii) IMMEDIATE SOURCE:
         (B) CLONE: Va2 5' PRIMER (xi) SEQUENCE DESCRIPTION: SEQ ID NO:19:

AGGTCGACGA ATGATGAAAT CCTTGAGAG                                      29

(2) INFORMATION FOR SEQ ID NO:20:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA to mRNA (iv) ANTI-SENSE: YES (vi) ORIGINAL SOURCE:
         (A) ORGANISM: Homo sapiens (vii) IMMEDIATE SOURCE:
         (B) CLONE: TCRa 3'antisense (xi) SEQUENCE DESCRIPTION: SEQ ID NO:20:

AATAGGTCGA CAGACTTGTC ACTGG                                           25

(2) INFORMATION FOR SEQ ID NO:21:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: homo sapiens (vii) IMMEDIATE SOURCE:
            (B) CLONE: V-D junction (xi) SEQUENCE DESCRIPTION: SEQ ID NO:21:

Ile Xaa Xaa Xaa Asn
1               5

(2) INFORMATION FOR SEQ ID NO:22:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: homo sapiens (vii) IMMEDIATE SOURCE:
            (B) CLONE: V-D junction (xi) SEQUENCE DESCRIPTION: SEQ ID NO:22:

Ile Gln Gly Xaa Asn
1               5

(2) INFORMATION FOR SEQ ID NO:23:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (v) FRAGMENT TYPE: internal (vi) ORIGINAL SOURCE:
            (A) ORGANISM: homo sapiens (vii) IMMEDIATE SOURCE:
            (B) CLONE: V-D junction (xi) SEQUENCE DESCRIPTION: SEQ ID NO:23:

Ile Gln Asn Pro
1           4